United States Patent [19]

Padden

[11] Patent Number: 4,536,390

[45] Date of Patent: Aug. 20, 1985

[54] COLLAPSIBLE FOAM AEROSOL HAIR PRODUCT

[75] Inventor: Timothy J. Padden, Racine, Wis.

[73] Assignee: S. C. Johnson & Son, Inc., Racine, Wis.

[21] Appl. No.: 467,725

[22] Filed: Feb. 18, 1983

[51] Int. Cl.³ ............................ A61K 7/06; A61K 9/12
[52] U.S. Cl. .............................. 424/47; 424/DIG. 1; 424/70; 424/78
[58] Field of Search ...................... 424/70, 47, DIG. 1

[56] References Cited

U.S. PATENT DOCUMENTS

| | | |
|---|---|---|
| 3,972,336 | 8/1976 | Nowak, Jr. et al. ......... 424/DIG. 1 |
| 4,223,009 | 9/1980 | Chakrabarti .................. 424/DIG. 1 |
| 4,243,657 | 1/1981 | Okumura et al. ............ 424/DIG. 1 |
| 4,272,511 | 6/1981 | Papantonion ................. 424/DIG. 1 |
| 4,397,836 | 8/1983 | Madrange et al. ........... 424/DIG. 2 |

*Primary Examiner*—Dale R. Ore

[57] ABSTRACT

An aerosol hair treating composition which forms a relatively stable yet collapsible foam comprising 3 to 90% by weight propellent and 97 to 10% by weight of an aqueous intermediate of 0.25 to 5% by weight polymer, 0.25 to 2% quaternary ammonium compound and water.

9 Claims, No Drawings

COLLAPSIBLE FOAM AEROSOL HAIR PRODUCT

BACKGROUND

This invention relates to a product for imparting holding and conditioning properties to the hair. More particularly, this invention relates to a product and method for delivering, holding and conditioning materials in a unique manner.

Conditioning agents have been applied to the hair in a variety of methods such as cream rinses, which are applied immediately after shampooing and rinsed out, pump sprays to remove tangles from the hair, etc. These materials were generally applied in the wet mode during or immediately after shampooing the hair. When applied as a cream rinse, the conditioning agent is mostly rinsed out of the hair, depositing some conditioning agent behind because of substantivity to the hair. Since the hair is rinsed after application of the conditioning agent, substantially more conditioning agent must be used than would otherwise be necessary to effectively condition the hair even with hair substantive conditioners.

Likewise, most products which are used for styling and holding the hair are applied in the dry mode after the hair has been set or arranged into the desired configuration. Typically, these materials, which are polymeric in nature, are applied either via an aerosol or pump spray to the hair. This may involve a substantial amount of overspray and also provides merely a surface hold to the hair.

Canadian Pat. No. 1,021,264 decribes a self-foaming shampoo and hair set composition. These compositions are anhydrous formulations which when applied to wet hair spontaneously foam. If the formulation includes a bodying and/or setting agent, this is also deposited. The object is to use high molecular weight polymers which are not suitable for use in aqueous systems.

U.S. Pat. No. 4,342,744 discloses hair treatment products which combine a conditioner and a setting aid. The polymers are quaternized and combined with a phosphate ester. These products are alcohol water systems and appear to be applied to the hair as liquids.

BRIEF DESCRIPTION OF THE INVENTION

It has been surprisingly found that conditioning and holding compositions can be applied to the hair using a relatively stable, collapsible aerosol foam. This foam is formed from an aerosol container and comprises a small percentage of a quaternary ammonium compound, a small percentage of a cationic or amine functional polymer, water and propellant. When this product is dispensed from an aerosol container, it forms a light, fluffy, dry foam which is relatively stable. However, upon application of mechanical energy to the foam, it quickly collapses such that when it is applied to the hair it will uniformly distribute the conditioning and holding compositions to the hair.

OBJECTS AND ADVANTAGES

It is, therefore, the primary object of the present invention to provide a composition which can be applied to the hair to impart conditioning and holding properties.

It is a further object of the present invention to provide a composition which can be applied to the hair as a dry feeling foam.

It is a still further object of the present invention to provide a composition which can be applied to the hair either in wet mode, dry mode or as a touch-up between shampooings.

It is a still further object of the present invention to provide a composition which can provide exceptional set and hold properties to the hair when styled with a curling iron or hot rollers.

It is a still further object of the present invention to provide a product which can be applied to dry hair without imparting substantial moisture to the hair, but at the same time adds sufficient moisture to aid in styling or curling the hair.

Still further objects and advantages of the composition of the present invention will become more apparent from the following detailed description thereof.

DETAILED DESCRIPTION OF THE INVENTION

The aerosol stable collapsible foam compositions of the present invention comprise from 10 to 97% by weight of an intermediate comprising from about 0.25 to 5% by weight of a high molecular weight polymer selected from the group consisting of cationic polymers, amine functional polymers and mixtures thereof; from about 0.25 to 2% by weight of a quaternary ammonium compound having the following formula:

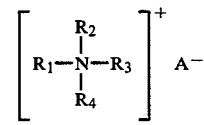

wherein $R_1$ is an alkyl group having from 8 to 16 carbon atoms, a mixture of alkyl groups having an average chain length of from 8 to 16 carbon atoms, or tallow if $R_2$ is a group having the formula $[CH_2-CH_2-O]_n-H$, $R_2$ is an alkyl group having from 8 to 16 carbon atoms, a mixture of alkyl groups having an average carbon atom chain length of from 8 to 16 carbon atoms, an alkyl group having from 1 to 4 carbon atoms, a group having the formula $[CH_2-CH_2-O]_n-H$, wherein n is a number from 2 to 16 and mixtures thereof, $R_3$ is an alkyl group having from 1 to 4 carbon atoms, a group having the formula $[CH_2-CH_2-O]_n-H$, wherein n is a number from 2 to 16 and mixtures thereof, $R_4$ is an alkyl group having 1 to 4 carbon atoms, benzyl and mixtures thereof and A is an anion; and the balance aqueous vehicle and from 90 to 3% by weight of a propellant.

The first component of the composition of the present invention is the high molecular weight polymer. By high molecular weight polymer is meant a polymer having a weight average molecular weight of greater than 10,000 and preferably greater than 50,000. These molecular weights can be determined by any variety of conventional methods including gel permeation chromotography and the like. Furthermore, since the composition of the present invention is designed to be used as a personal care product, the polymer should have low toxicity. Suitable polymers also must be water-soluble and be stable at a pH of less than 7. Suitable polymers include Onamer M from Onyx which has the following general formula:

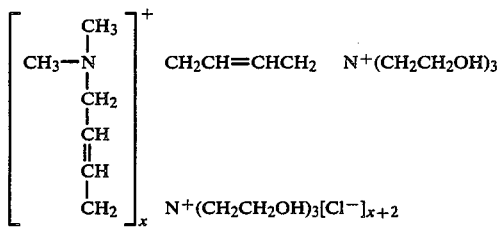

Mirapol A-15 from Miranol which has the formula,

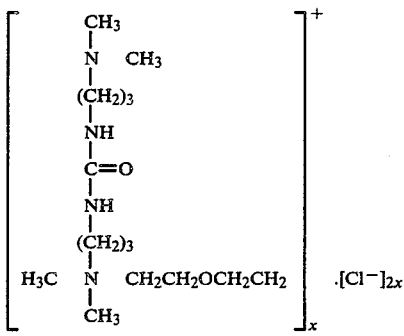

Celquat H-60 and Celquat L-200, which are copolymers of hydroxyethyl cellulose and diallyl ammonium chloride, the copolymer of acrylamide and betamethacryl oxyethyl methylamine ammonium methyl sulfate, sold under the tradenames Catamer Q and Reten, the polymers of dimethyl diallyl ammonium chloride, the polymeric quaternary ammonium salts of acrylamide and dimethyl diallyl ammonium chloride, such as those sold under the tradename Merquat 550, the polymeric quaternary ammonium salts or methyl and stearyl dimethyl amino ethyl methacrylate quaternized with dimethyl sulfate, polydimethylaminoethyl methacrylate quaternized with methyl bromide, the quaternary ammonium polymer formed by the reaction of dimethyl sulfate and a copolymer of vinyl pyrrolidone and dimethyl aminoethylmethacrylate such as those sold under the tradenames Gafquat 734 and 755 from GAF, the polymeric quaternary ammonium salt prepared by the reaction of ethyl methacrylate abietyl methacrylate diethylaminoethyl methacrylate copolymer quaternized with dimethyl sulfate, polymers prepared from vinyl pyrrolidone and dimethyl aminoethylmethacrylate monomers sold under the trade names Copolymer 845, Copolymer 937 and Copolymer 958 available from GAF and the like.

The above polymers are representative of cationic polymers which have sufficient water solubility and sufficiently low toxicity and are stable at a pH of less than 7. As noted above, the polymers should be present in the intermediate of the composition of the present invention in an amount of from 0.25 to 5%. It is preferred that from 1 to 3% polymer be used.

The most preferred polymers are the copolymers of vinyl pyrrolidone and dimethylaminoethylmethacrylate quaternized with dimethyl sulfate.

The function of the polymers in the composition of the present invention is two-fold. First, the polymers add structural strength to the foam of the present invention. These polymers must provide sufficient integrity of these foams so that they are stable when dispensed onto a surface, but yet not provide such integrity to the foam such that would prevent the foam from rapidly being collapsed upon application of mechanical force. These polymers also provide a hair setting function such that upon application of heat or otherwise forming the hair into the desired configuration, the polymers will act to hold the hair in place.

The second component of the composition of the present invention is a quaternary ammonium compound having the following formula:

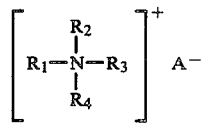

wherein $R_1$ is an alkyl group having from 8 to 16 carbon atoms, a mixture of alkyl groups having an average chain length of from 8 to 16 carbon atoms, or tallow if $R_2$ is a group having the formula $[CH_2-CH_2-O]_nH$, $R_2$ is an alkyl group having from 8 to 16 carbon atoms, a mixture of alkyl groups having an average carbon atom chain length of from 8 to 16 carbon atoms, tallow, an alkyl group having from 1 to 4 carbon atoms, a group having the formula $[CH_2-CH_2-O]_n-H$, wherein n is a number from 2 to 16 and mixtures thereof, $R_3$ is an alkyl group having from 1 to 4 carbon atoms, a group having the formula $[CH_2-CH_2-O]_n-H$, wherein in is a number from 2 to 16 and mixtures thereof, $R_4$ is an alkyl groyp having 1 to 4 carbon atoms, benzyl and mixtures thereof and A is an anion. These quaternary ammonium compounds have two functions, namely: (1) acting as a conditioning agent to soften, to act as an anti-static agent and the otherwise provide manageability to the hair, and (2) to provide the surfactancy necessary to create the stable collapsible foam. Accordingly, any quaternary ammonium compound which will foam in water to a reasonable extent can be utilized in the composition of the present invention.

Further, it has been found that the preferred quaternary ammonium compounds have alkyl chains of $C_{16}$ and below. It is recognized that quaternary ammonium compounds often are made from naturally occurring substances which include a wide variety of chain length material. For the purposes of this application, the chain length should be considered as the average chain length of the alkyl groups. Furthermore, for toxicity reasons, it is desired to use quaternary ammonium compounds having a chain length of at least $C_8$ for the higher alkyl chains. Also, it has been found that both mono and di-higher alkyl ammonium compounds can be utilized.

Quaternary compounds are also often made from tallow containing amines. By the term tallow is meant a mixture of alkyl and alkenyl groups having from 14 to 18 carbon atoms. Typical analysis of tallow chain length yield: C—saturated—5%; C-16 saturated—30%; C-18 saturated—20% and C-18 unsaturated—45%. Quaternary compounds containing a tallow group can only be used in the compositions of the present invention if there is also at least one ethoxylated group in the compound.

It has also been found that ethoxylated quaternary compounds such as ethyl bis(polyhydroxyethyl) tallow ammonium ethyl sulfate can be used as the quaternary compound. It is preferred that the degree of ethoxylation be between 6 and 30 moles ethylene oxide.

The preferred quaternary ammonium compounds are the mono- and di-$C_8$ to $C_{16}$ alkyl ammonium compounds. Typically, the other groups substituted on the nitrogen atom are lower alkyl, i.e., 1–4 carbon atoms, such as methyl, ethyl, etc. or benzyl group. It has been found that these groups can be utilized without inhibiting the conditioning and/or foaming properties required to successfully operate in the compositions of the present invention.

Suitable quaternary ammonium compounds include cetyl trimethyl ammonium chloride, cetyl trimethyl ammonium methyl sulfate, dicetyl methyl benzyl ammonium chloride, etc.

Generally, it has been found that from 0.25 to 2% of cationic quaternary ammonium compound should be used in the compositions of the present invention. It is preferred that from 0.5 to 1.5% cationic quaternary ammonium compound is utilized. The above ranges define the most operative compositions. At below 0.25% insufficient conditioning and surfactancy is evidenced, while above 2% both toxicity and cost considerations become important.

The compositions of the present invention also include substantial quantities of water. The balance of the intermediate compositions is water. Generally, for the purposes of solubility and foaming, deionized water will be utilized. Although water is used as the filler or carrier compound, small quantities of other components such as preservatives, perfumes and the like may be included. However, large quantities of other materials such as lower, i.e., $C_1$–$C_4$, alcohols should not be included as they can have a deleterous effect on the hair. A small amount of alcohol, less than 10%, may be included in the compositions of the present invention; however, it is preferred that the compositions contain no lower alcohols.

The composition of the present invention also include a substantial amount of propellent. Generally, it has been found that from 90% to 3% by weight propellent should be mixed with 10% to 97% by weight of the above aqueous intermediate. It is preferred that the composition include from 70% to 30% by weight of propellent and 30% to 70% by weight of aqueous intermediate. It is most preferred that between 30% to 50% propellent be utilized and 70% to 50% by weight of aqueous intermediate.

As propellents, any of the standard liquified propellent materials commonly used can be incorporated. These include the hydrocarbon propellents such as propane, butane, isobutane, etc. Also, chlorofluoronated hydrocarbons can be utilized, although with these materials in an aqueous environment, corrosion can be a consideration.

The compositions of the present invention also may include small conventional amounts of perfumes and preservatives, as well as corrosion inhibitors. Generally, these materials are present in less than 5% by weight and are chosen so that they do not affect the overall performance of the product in a negative manner.

The compositions of the present invention are packaged within a conventional aerosol container. These aerosol containers are fitted with standard dip tube and valving such that a foam will be produced upon actuation of the valve. Since the intermediate and the propellent are not always completely compatible over long periods of time, a micro dip tube is preferred, since this minimizes the amount of free propellent which might float on top of the aqueous intermediate in the dip tube.

Further, some headspace must be provided so that the aqueous intermediate and propellent can be redispersed by shaking before use. For purposes of corrosion, it is preferred to utilize lined aluminum aerosol containers.

The compositions of the present invention can be used in the following manner: The hair may either be damp or dry; a small amount of composition is dispensed from the container on to the hand of the user in the form of a light airy foam; the user then distributes the foam through the hair using their hands; the hair is then styled or set as usual.

The compositions of the present invention will now be illustrated by way of the following examples which are for the purposes of illustration only and are in no way considered as limiting.

EXAMPLE 1

The following formulation was prepared by adding the compounds to the deionized water in the order given. These materials were then mixed to give the following formulation:

| | |
|---|---|
| Cetyl trimethyl Ammonium chloride (25% solution) (Variquat E228) | 3.00 Parts |
| Preservative (Kathon CG) | 0.04 Parts |
| Polyquaternium-11 (Gafquat 755N)[1] | 8.00 Parts |
| Perfume | 0.10 Parts |
| Deionized Water | 88.86 Parts |

[1]Gafquat 755N is a quaternary ammonium polymer formed by the reaction of dimethyl sulfate and a copolymer of vinyl pyrrolidone and dimethyl aminoethylomethacrylate having a weight average molecular weight of greater than 1,000,000, and having a solids content of about 19%, available from GAF.

The above intermediate was filled into aluminum epoxy-lined aerosol cans using 112.7 grams of the above intermediate and 135.5 ml. of A-46 propellent (a mixture of 15.4 weight percent propane and 84.6 weight percent isobutane). The aerosol cans were fitted with an aerosol valve with a micro dip tube.

Upon actuation, the product produced a light airy dry foam which was easily broken upon application of mechanical energy. This product, when applied to the hair, quickly dispersed throughout the hair and provided good manageability and ability to hold a curl.

EXAMPLES 2–4

A series of formulations were prepared varying the amount of quaternary. The compositions had the following formula and were prepared by adding the compounds in order to the deionized water. The amount of quaternary and water is shown in Table 1.

| | |
|---|---|
| Cetyl trimethyl Ammonium chloride (25% solution) (Variquat E228) | $V_2$ Parts |
| Preservative (Kathon CG) | 0.04 Parts |
| Polyquaternium-11 (Gafquat 755N)[1] | 8.00 Parts |
| Perfume | 0.10 Parts |
| Deionized Water | $V_2$ Parts |

[1]See Example 1
[2]V - Amount Varies - See Table 1

TABLE 1

| Example | Quat | Water |
|---|---|---|
| 2 | 4.00 | 87.86 |
| 3 | 5.00 | 86.86 |
| 4 | 6.00 | 85.86 |

The above intermediates were then filled in to aerosol cans in a manner similar to Example 1 using 77 grams of intermediate and 92 ml. of A-46 propellent.

Each of these products when dispensed had similar foam in that they were essentially dry fluffy foams which were readily dispersed upon application of shear energy.

EXAMPLES 5–7 AND COMPARATIVE EXAMPLE 1

Intermediate formulations were prepared by adding the chemicals in the order listed below to the deionized water. The amount of cetyl triammonium chloride and deionized water was varied as set forth in Table 2.

| | |
|---|---|
| Cetyl Trimethyl Ammonium Chloride (25% Solution) (Variquat E228) | $V_2$ Parts |
| Preservative (Kathon CG) | 0.04 Parts |
| Polyquaternium-11 (Gafquat 755N)[1] | 8.00 Parts |
| Perfume | 0.15 Parts |
| Deionized Water | $V_2$ Parts |

[1]See Example 1
[2]V - Amount Varies - See Table 2

TABLE 2

| Example | Quat | Water |
|---|---|---|
| 5 | 4.00 | 85.81 |
| 6 | 3.00 | 86.81 |
| 7 | 2.00 | 87.81 |
| CE1 | 1.00 | 88.81 |

Each of the formulations were pressurized using 77 grams of intermediate with 91 ml. of A-46 propellent. The formulation of comparative Example 1 was unacceptable since the foam was unstable when being dispensed. The formulation of Example 7 was marginally satisfactory in that the bubble size was slightly larger and tended to break slightly upon standing. The formulations of both Examples 5 and 6 were acceptable giving a light airy foam which readily broke upon application of sheer force. Hair tresses treated with formulations of Example 5 through 7 showed little evidence of fly-away and held a set applied from a hot curling iron.

EXAMPLES 8 & 9 AND COMPARATIVE EXAMPLES 2 & 3

A non-pressurized intermediate formulation having the following composition was prepared:

| | |
|---|---|
| Cetyl Trimethyl Ammonium Chloride (25% Solution) (Variquat E228) | 3.00 Parts |
| Preservative (Kathon CG) | 0.04 Parts |
| Polyquaternium-11 (Gafquat 755N)[1] | 8.00 Parts |
| Perfume | 0.15 Parts |
| Deionized Water | 88.81 Parts |

[1]See Example 1

This intermediate was then pressurized with A-46 propellent using various ratios as set forth in Table 3.

TABLE 3

| Example | Intermediate | Propellant A-46 |
|---|---|---|
| 8 | 77 gms. | 70 ml |
| 9 | 77 gms. | 50 ml |
| CE2 | 77 gms. | 30 ml |
| CE3 | 77 gms. | 10 ml |

When dispensed from an aerosol container, the pressurized formulations of Examples 8 and 9 were dry, fluffy foams which did not appreciably stick to the hand. The formulation of comparative Example 2 was not dispensed as a dry, fluffy foam and struck to the hand. Furthermore, this formulation was dispensed as a liquid if it was not shaken well. The formulation of comparative Example 3 produced an unacceptable, very dense, pasty foam. Furthermore, only a small amount of this foam was produced.

EXAMPLE 9

A formulation having the following composition was prepared:

| | |
|---|---|
| Varstat 66[1] | 1.04% |
| Kathon CG | 0.04% |
| Polyquaternium-11 (Gafquat 755N)[2] | 8.00% |
| Perfume | 0.15% |
| Deionized Water | 90.77% |

[1]Varstat 66 - Ethyl bis(polyhydroxyethyl) tallow ammonium ethylsulfate - available from Sherex Corporation - approximately 90% quaternary solution.
[2]See Example 1

The above formulation was then pressurized by mixing 77 gms of the intermediate with 50 ml of A-46 propellent. When dispensed from an aerosol container, the composition produced a good foam with little stickiness and a conditioned feel on the skin.

EXAMPLE 11

A non-pressurized intermediate having the following formulation was prepared:

| | |
|---|---|
| Cetyl trimethylammonium methylsulfate- (26.0% Solution) | 3.0% |
| Preservatives | 0.04% |
| Polyquaternium - 11 (Gafquat 755N)[1] | 8.0% |
| Perfume | 0.10% |
| Deionized Water | 88.86% |

[1]See Example 1

74.1 grams of the above intermediate was filled into an aerosol can along with 89.1 ml of A-46 propellent. The product on actuation formed a dry foam with good bubble size. When applied to the hair, the formula seemed to dampen the hair and was able to hold a set with a curling iron.

EXAMPLES 12 & 13 & COMPARATIVE EXAMPLE 4

A series of non-pressurized intermediates as set forth in Table 4 were prepared. Each of these intermediates were blended by incorporating 77 grams of the intermediate along with 92 ml of A-46 propellent.

TABLE 4

| Example | 11 | 12 | CE5 |
|---|---|---|---|
| Monaquat TG[1] | 4% | — | — |
| Variquat E228[2] | — | 6% | — |
| Adogen 470E[3] | — | — | 3% |
| Copolymer 845[4] | 5% | 5% | 5% |
| Deionized Water | 91% | 89% | 92% |

[1]Monaquat TG - 30% Solution - Alkyl poly hydroxy substituted ammonium chloride available from Mona Industries.
[2]Variquat E228 - 25% Solution - See Example 1
[3]Adogen 470E - 75% Solution - di tallow dimethyl ammonium chloride - Sherex Chemical.
[4]Copolymer 845 - A polymer prepared from vinylpyrrolidone and dimethylaminoethylmethacrylate molecular weight of about 1,000,000. Available from GAF.

Upon actuation, the formulations of Examples 11 and 12 formed acceptable foams which were fairly dry and stable. However, Comparative Example 5, which includes a quaternary having a tallow alkyl group but no ethoxylated groups, forms a foam which initially puffs up, but then begins collapsing immediately without any application of pressure. The compositions of Examples 11 and 12 when applied to hair tresses performed adequately and gave good hold.

What I claim is:

1. A hair treating composition to be dispensed from a pressurized aerosol container as a stable, collapsible foam, said composition comprising:

A. from about 10 to 97% by weight of an aqueous intermediate comprising:
  (i) from about 0.25 to 5% by weight of a high molecular weight polymer selected from the group consisting of cationic polymers, aminefunctional polymers and mixtures thereof;
  (ii) from about 0.25 to 2% by weight of quaternaryamonium compound having the following formula:

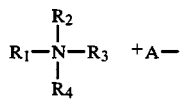

Wherein $R_1$, is a alkyl group having from 8 to 16 carbon atoms, a mixture of alkyl groups having an average chain length of from 8 to 16 carbon atoms or tallow if $R_2$ is a group having the formula $[CH_2—CH_2—O]_nH$, $R_2$ is an alkyl group having from 8 to 16 carbon atoms, a mixture of alkyl groups having an average carbon atom chain length of from 8 to 16 carbon atoms, an alkyl group having from 1-4 carbon atoms, a group having the formula $[CH_2—CH_2—O]_nH$, wherein $n$ is a number from 2 to 16 and mixtures thereof, $R_3$ is an alkyl group having from 1 to 4 carbon atoms, a group having the formula $[CH_2—CH_2—O]_n—H$, wherein $n$ is a number from 2 to 16 and mixtures thereof, $R_4$ is an alkyl group having 1 to 4 carbon atoms, benzyl and mixtures thereof and A is an anion;
  (iii) and the balance water; and (B) from about 90 to 3% by weight of a propellant and (C) less than 10% alcohol having 1–4 carbon atoms, whereby said composition is essentially alcohol free.

2. The composition of claim 1 wherein the polymer is selected from the group consisting of polymeric ammonium salts prepared by the reaction of dimethyl sulfate and a copolymer of vinyl pyrrolidone and dimethylaminoethylmethacrylate, a polymer prepared from vinyl pyrrolidone and dimethylaminoethylmethacrylate; and mixtures thereof.

3. The composition of claim 1 wherein the quaternary ammonium compound is selected from the group consisting of cetyltrimethyl ammonium chloride, cetyltrimethyl ammonium methyl sulfate, dicetylmethylbenzyl ammonium chloride, ethyl bis(polyhydroxyethyl)-tallow ammonium ethyl sulfate and mixtures thereof.

4. The composition of claim 1 wherein the propellent is selected from the group consisting of propane, butane, isobutane, and mixtures thereof.

5. The composition of claim 1 wherein the polymer has a weight average molecular weight of greater than 50,000.

6. The composition of claim 1 wherein the polymer is present in an amount of from about 1 to 3% by weight.

7. The composition of claim 1 wherein the quaternary ammonium compound is present in an amount of from about 0.5 to 1.5% by weight.

8. The composition of claim 1 wherein the aqueous intermediate is present in an amount of from about 10 to 90% by weight and the propellent is present in an amount of from about 90 to 10% by weight.

9. The composition of claim 1 wherein the aqueous intermediate is present in an amount of from about 20 to 80% by weight and the propellent is present in an amount of from about 80 to 20% by weight.